(12) United States Patent
Lam et al.

(10) Patent No.: US 8,338,553 B2
(45) Date of Patent: Dec. 25, 2012

(54) SOLVATOCHROMIC MOLECULARLY IMPRINTED POLYMER FOR CHEMOSENSING

(75) Inventors: Hon-Wah Lam, Hong Kong (HK); Chengbin Gong, Hong Kong (HK)

(73) Assignee: City University of Hong Kong, Kowloon (HK)

( * ) Notice: Subject to any disclaimer, the term of this patent is extended or adjusted under 35 U.S.C. 154(b) by 131 days.

(21) Appl. No.: 12/459,432

(22) Filed: Jul. 1, 2009

(65) Prior Publication Data
US 2011/0003397 A1    Jan. 6, 2011

(51) Int. Cl.
G01N 21/76    (2006.01)
G01N 21/78    (2006.01)

(52) U.S. Cl. .......... 526/263; 436/77; 436/164; 436/172; 546/339

(58) Field of Classification Search ........................ None
See application file for complete search history.

(56) References Cited

U.S. PATENT DOCUMENTS

| | | | |
|---|---|---|---|
| 4,841,058 A * | 6/1989 | Endo et al. | 546/257 |
| 6,749,811 B2 | 6/2004 | Murray | |
| 6,872,786 B2 | 3/2005 | Murray et al. | |

FOREIGN PATENT DOCUMENTS
WO    WO 01/90228 A1    11/2001

OTHER PUBLICATIONS

Manesiotis, P. et al. "An enantioselective imprinted receptor for Z-glutamate exhibiting a binding induced color change," Chem. Commun. 2004, 2278-2279.*

Wu, X. "Selective phosphate recognition by triurea-based molecularly imprinted polymers," Abstract, 233rd A.C.S. National Meeting, Chicago, IL, Mar. 25, 2007.*

Gallego-Gallegos, M. et al. "Synthesis and evaluation of molecularly imprinted polymers for organotin compounds: a screening method for tributyltin detection in seawater," Analytica Chimica Acta 531 (2005) 33-39.*

Lapucha, A. R. "Heterocyclic Analogs of Stilbenes: Reactions of (E) 4-Azastilbenes with Polymethylene Dibromides," Polish Journal of Chemistry, 1987, 61, 563-567.*

Dickert et al., "Modifying polymers by self-organisation for the mass-sensitive detection of environmental and biogeneous analytes," Science Direct, Sensors and Actuators B 100 (2004) 112-116.

(Continued)

Primary Examiner — Yelena G Gakh
Assistant Examiner — Michelle Adams
(74) Attorney, Agent, or Firm — Leydig, Voit & Mayer, Ltd.

(57) ABSTRACT

Disclosed are a solvatochromic functional monomer having the chemical structure

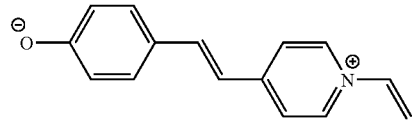

and a process for preparing the same. The solvatochromic functional monomer can be used for fabrication of molecularly imprinted polymer based (MIP-based) solvatochromic chemosensors. This involves the incorporation of the solvatochromic functional monomer as reporter into the molecularly imprinted polymer. The solvatochromic functional monomers as reporters signal the analyte-to-receptor displacing event within the receptor sites without the need for intermolecular interaction between the analyte and the receptor.

6 Claims, 13 Drawing Sheets

OTHER PUBLICATIONS

Whitcombe et al., "Imprinted Polymers," *Advanced Materials*, 2001, 13(7), 467-478.

Ye et al., "Molecularly imprinted polymers as antibody and receptor mimics for assays, sensors and drug discovery," *Anal. Bioanal. Chem.*, (2004) 378: 1887-1897.

Bao, et al., "L-Tartaric acid assisted binary organogel system: strongly enhanced fluorescence induced by supramolecular assembly," *Org. Biomol. Chem.*, 2005, 3, 2508-2512.

Greene et al., "Colorimetric Molecularly Imprinted Polymer Sensor Array using Dye Displacement," *J. Am. Chem. Soc.*, (2005), 127, 5695-5700.

Haupt, "Molecularly imprinted polymers in analytical chemistry," *Analyst*, (2001) 126, 747-756.

Mauriz et al., "Optical immunosensor for fast and sensitive detection of DDT and related compounds in river water samples," Biosensors and Bioelectronics 22 (2007) 1410-1418.

Graham et al., "Development and Characterization of Molecularly Imprinted Sol-Gel Materials for the Selective Detection of DDT," *Analytical Chemistry*, vol. 74, 2002, 458-467.

Koopmans et al., "Color Change of $N'$-Isopropylacrylamide Copolymer Bearing Reichardts Dye as Optical Sensor for Lower Critical Solution Temperature and for Host-Guest Interaction with β-Cyclodextrin." *J. Am. Chem. Soc.*, (2007), 129, 3502-3503.

\* cited by examiner

Chlordane

γ-BHC - Lindane

Mirex

Polychlorinated biphenyls - PCBs p,p'-DDT

Polybrominated diphenyl ethers (PBDEs)
\* - possible site of bromination

Dioxins
\* - possible site of chlorination

Gradually changes from red to greenish yellow in color

SOLVATOCHROMIC MOLECULARLY IMPRINTED POLYMER FOR CHEMOSENSING

TECHNICAL FIELD

The present invention relates to a solvatochromic functional monomer having the following chemical structure:

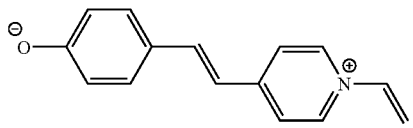

and a process for preparing the solvatochromic functional monomer. The present invention also relates to the use of the solvatochromic functional monomer for fabrication of a molecularly imprinted polymer based (MIP-based) solvatochromic chemosensor. The invention further relates to a molecularly imprinted polymer based (MIP-based) solvatochromic chemosensing approach.

BACKGROUND OF THE INVENTION

In the fields of chemical and medical sciences, pharmacy and biotechnology, especially in the fields of environmental monitoring and food safety control, there is an increasing demand for the rapid analysis and real-time responses of specific substances such as certain contaminants in complex mixtures of related substances.

A conventional chemosensing approach or a conventional chemosensor which selectively recognizes and reversibly binds targeted molecular entities and yields measurable signals can be used for the purposes discussed above. The term of chemosensing refers to the recognition of targeted analytes via molecular-level sensors. In general, a chemosensor consists of (1) a molecular receptor, which can recognize and bind to its targeted analytes, and (2) a signal transducer that signals this binding event to the outside world. However, the specificity of conventional chemosensing approaches or chemosensors is usually limited to functional group level.

Molecularly imprinted polymer based (MIP-based) chemosensing approach or an MIP-based chemosensor selectively recognizes and reversibly binds targeted molecular entities and yields measurable signals, in a similar way as conventional chemosensing, except that the molecularly imprinted polymer based (MIP-based) chemosensor recognizes the molecular shape of its target analyte by molecular imprinting rather than chemical functionality recognition.

The term of molecularly imprinting refers to the induction of highly specific binding sites in synthetic polymers (referred to as the molecularly imprinted polymers—MIPs) by template-directed cross-linking of functional monomers. The process of molecular imprinting is schematically represented by FIG. 1.

As shown in FIG. 1, molecular imprinting approach involves formation of a template-functional monomer aggregate between a given template molecule and functional monomers (for example, functional monomers for non-covalent interactions, functional monomers for covalent interactions, and functional monomers for chelating interactions) in an appropriate solvent. The template-functional monomer aggregate is then fixed by cross-linking of functional monomers with cross-linkers. Subsequent removal of the template leaves binding sites within the polymer possessing both shape and the correct orientation of functional groups to allow specific re-binding of the template molecule and selective recognition of the imprint molecule.

In respect of the prior molecular imprinting strategies, which have been proposed for molecularly imprinted polymer based (MIP-based) chemosensing purpose, the interaction between functional monomers and the analytes is required in the molecular imprinting process as well as the subsequent analytes re-binding and chemosensing processes. The subsequent analyte's re-binding and chemosensing processes usually require the existence of some sort of intermolecular interaction between the target analytes and the signal transducer moiety. In other words, the subsequent analyte's re-binding and chemosensing process requires the existence of some sort of intermolecular interaction between the target analytes and the functional monomer. Therefore, the selection of appropriate signal transducer or functional monomer is important, which mainly depends on the type of intermolecular interaction between the target analytes and the signal transducer moiety, such as hydrogen bonding, dipole-dipole interactions and electron transfer.

However, analytes which lack the ability of intermolecular interaction with the signal transducer or functional monomer cannot be easily detected by this convenient molecularly imprinted polymer based (MIP-based) chemosensing approach because the analytes cannot intermolecularly interact with the signal transducer or functional monomer.

SUMMARY OF THE INVENTION

To solve the problem, the present invention provides a solvatochromic functional monomer which can be used for incorporation as signal transducer to form a reporter site within the molecularly imprinted polymers (MIPs). The solvatochromic functional monomer has the following chemical structure.

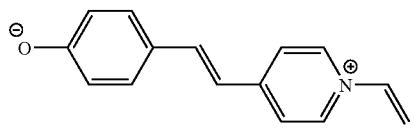

The solvatochromic functional monomer exhibits a media polarity. The media polarity of the solvatochromic functional monomer changes when a target analyte enters into the reporter site within the molecularly imprinted polymers. This solvatochromic functional monomer is highly sensitive to the change of the media polarity of receptor micro-environment when an analyte enters into the reporter site by displacing solvent molecules originally accommodated inside the receptor site. The displacing event results in the significant change of color and luminescent properties of the solvatochromic functional monomer, wherein the change can be detected easily, even by naked eyes. As a result, the intermolecular interaction between the target analytes and the functional monomer is not required. Therefore, the analytes which lack the ability of intermolecular interaction can be easily detected by the molecularly imprinted polymer based (MIP-based) chemosensing approach.

The present invention also provides a process for preparing the solvatochromic functional monomer, the process comprises the following steps of:
(a) coupling 4-hydroxybenzaldehyde with 4-methylpyridine by using a dehydrated reagent for obtaining 4-[(E)-2-(4-pyridinyl)ethenyl]phenol;

(b) inserting a terminal vinyl group to a pyridine ring of 4-[(E)-2-(4-pyridinyl)ethenyl]phenol obtained in step (a) by refluxing with an allylic halide for obtaining 4-[(E)-2-(4-hydroxyphenyl)ethenyl]-1-allylpyridinium; and (c) deprotonating a phenolic group of the 4-[(E)-2-(4-hydroxyphenyl)ethenyl]-1-allylpyridinium obtained in step (b) by using an initiator for obtaining the solvatochromic functional monomer of the present invention.

Preferably, the dehydrated reagent used in step (a) is acetic anhydride.

Preferably, the allylic halide used in step (b) is allyl bromide.

Preferably, the initiator used in step (c) is sodium methoxide.

The synthetic route of the solvatochromic functional monomer is represented by FIG. 2.

The present invention further discloses a use of the solvatochromic functional monomer for fabricating molecularly imprinted polymer based (MIP-based) solvatochromic chemosensor for chemosensing of a target analyte which lacks the ability of intermolecular interaction with the solvatochromic functional monomer. The molecularly imprinted polymer based (MIP-based) solvatochromic chemosensor is prepared by generic molecular imprinting technique, wherein the functional monomer used in preparation is solvatochromic functional monomer of the present invention. The process for preparing a molecularly imprinted polymer based (MIP-based) solvatochromic chemosensor comprises steps of:

(a) polymerizing a solvatochromic functional monomer and a template for obtaining a molecularly imprinted polymer; and (b) removing the template from the molecularly imprinted polymer obtained in step (a) for obtaining a molecularly imprinted polymer based solvatochromic chemosensor.

Furthermore, the present invention discloses a molecularly imprinted polymer based (MIP-based) solvatochromic chemosensing approach. This approach involves the combination of solvatochromism and molecular imprinting technique in chemosensing of the target analytes. In particular, this involves incorporation of the solvatochromic functional monomer as reporters into the molecularly imprinted polymer.

On one hand, because of the combination of solvatochromism and molecular imprinting technique, there is no requirement for an analyte to intermolecularly interact with the solvatochromic reporter moiety within the molecularly imprinted polymers. On the other hand, the MIP-based solvatochromic chemosensing approach signals the solvent displacement event induced by the receptor-analyte re-binding into physically measurable forms, e.g. the change in color and luminescence of the molecularly imprinted polymer, which can be easily detected. The approach comprises the following steps of:

(a) contacting the molecularly imprinted polymer incorporating the solvatochromic functional monomer with a target analyte; and (b) detecting a change in an optical property of the molecularly imprinted polymer when the target analyte enters into the receptor site within the molecularly imprinted polymer.

Preferably, the target analyte enters into the receptor site by displacing with a molecule originally accommodated inside the receptor site.

Preferably, the solvatochromic functional monomer incorporated into the molecularly imprinted polymer is the solvatochromic functional monomer of the present invention.

BRIEF DESCRIPTION OF THE DRAWINGS

The embodiments of the invention will now be described, by way of example with reference to the drawings of which.

DETAILED DESCRIPTION OF THE PREFERRED EMBODIMENT OF THE INVENTION

The best mode for carrying out the present invention is described in detail.

Figure 3:
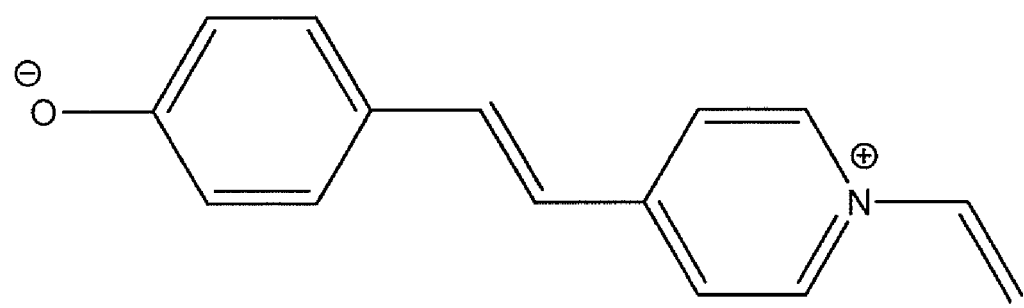
FIG. 3 depicts a chemical structure of the solvatochromic functional monomer of the present invention.

According to the invention, a solvatochromic functional monomer is provided which has the following chemical structure (reference is made to FIG. 3).

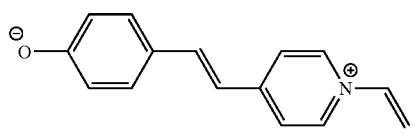

The solvatochromic functional monomer is used for the preparation of a molecularly imprinted polymer based (MIP-based) solvatochromic chemosensor. Advantageously, the solvatochromic functional monomer responds to the change of the media polarity of receptor micro-environment within the molecularly imprinted polymers (MIPs) in a form of change of color and luminescence properties of the overall MIPs which incorporated the solvatochromic functional monomer.

The invention also discloses a MIP-based solvatochromic chemosensing approach, which involves the combination of solvatochromism and molecular imprinting technique in chemosensing of the target analytes. In particular, this involves the incorporation of solvatochromic functional monomer as reporter into the molecularly imprinted polymers (MIPs).

Now we describe the experimental synthesis of the solvatochromic functional monomer in details as follow.

Materials and Apparatus

The details of materials and apparatus used in the synthesis of the solvatochromic functional monomer are set out as below.

4-Hydroxybenzaldehyde (98%), 4-methylpyridine (4-picolin, 98%), acetic anhydride (98%), tetrabutylammonium hexafluorophosphate (TBAPF) (98%), tetrabutylammonium iodide (TBAI) (98%), trimethylolpropane trimethacrylate (TRIM), 1-azobiscyclo-hexanecarbonitrile (ABCN) and tributyltin (TBT) chloride were purchased from Aldrich. ABCN was recrystallized from methanol before use. Allyl bromide (99%) was purchased from Acros. Tetramethylammonium chloride (TMAC) (98%) was purchased from Merck. Tetrabutylammonium bromide (TBAB) (98%) was purchased from International Lab. 4-Methylpyridine (4-picolin, 98%) was redistilled before use. All other chemicals were used without further purification. All solvents used were of analytical reagent grade and were obtained from Lab-Scan Analytical Sciences and BDH.

$^1$H NMR and $^{13}$C NMR spectra were measured by a Varian YH300 300 MHz superconducting magnet high fields NMR spectrometer using tetramethylsilane (TMS) as the internal reference. Infrared spectra in the range 500-4000 cm$^{-1}$ were recorded on a Perkin Elmer Model FTIR-1600 spectrometer. Luminescent spectra were measured by a Flurolog TCSPC Horiba Jobin Yvon (FL-1065) spectrofluorometer with a build-in magnetic stirrer. Mass spectra were measured by a PE SCIEX AP1365 LC/MS/MS system.

(a) Synthesis of 4-[(E)-2-(4-pyridinyl)ethenyl]phenol

The step (a) of the synthesis of the solvatochromic functional monomer is the synthesis of 4-[(E)-2-(4-pyridinyl) ethenyl]phenol.

In a nitrogen atmosphere, 4-methylpyridine (12.1 mL, 0.15 mol) was added dropwise to a solution of 4-hydroxybenzaldehyde (16.0 g, 0.13 mol) in 30 mL of acetic anhydride. The mixture was refluxed for 12 h-24 h. The mixture was then poured into 300 mL of ice water and stirred for 1 h to hydrolyze the excess acetic anhydride. The precipitate obtained was filtered, washed with ice water and recrystallized from ethanol. The recrystallized product was then refluxed with 150 mL of ethanol and 7.0 g of potassium hydroxide for 90 min to obtain a dark solution. Addition of acetic acid precipitated out the yellow crude 4-[(E)-2-(4-pyridinyl)ethenyl]phenol which was collected by filtration and washed with deionized water and dried over a freeze-drier. Yield 9.6 g, 37.2%. The NMR results of the intermediate product are as follows.

1H NMR (300 MHz, d6-DMSO), δ (ppm): 9.83 (s, broad, 1H), 8.47 (d, 2H), 7.47 (bm, 5H), 7.02 (d, 1H), 6.79 (d, 2H). 13C-NMR (300 MHz, d6-DMSO), δ (ppm): 158.95, 150.58, 145.50, 133.75, 127.35, 127.85, 123.13, 121.17, 116.37. GC-MS: m/z 197.

As a result, 4-[(E)-2-(4-pyridinyl)ethenyl]phenol is obtained by coupling 4-methylpyridine with 4-hydroxybenzaldehyde by using a dehydrating reagent. The dehydrating reagent used is this step (a) is acetic anhydride.

(b) Synthesis of 4-[(E)-2-(4-hydroxylphenyl)ethenyl]-1-allylpyridinium bromide

The step (b) of the synthesis of solvatochromic functional monomer is the synthesis of 4-[(E)-2-(4-hydroxylphenyl) ethenyl]-1-allylpyridinium bromide.

To a stirred solution of 4-[(E)-2-(4-pyridinyl)ethenyl]phenol (4.0 g, 20 mmol) in 60 mL of dried acetonitrile at 60° C., allyl bromide (2.8 mL, 30 mmol) in 20 mL of acetonitrile was added dropwise within 20 min. The mixture was then refluxed for 12 h-24 h. The color of the mixture turned from blood red to orange. The mixture was then cooled room temperature and the precipitate collected by filtration. The yellow solid collected was washed with acetonitrile and hexane. Yield 6.0 g, 94.3%. MS-Q1:(m/z) 237.8. The NMR results of the intermediate product are as follows.

1H NMR (300 MHz, d6-DMSO), δ (ppm): 10.22 (s, broad 1H), 8.83 (d, 2H), 8.18 (d, 2H), 7.98 (d, 1H), 7.63 (d, 2H), 7.31 (d, 1H), 6.88 (d, 2H), 6.11-6.23 (m, 1H), 5.42-5.45 (m, 2H), 5.13 (d, 2H). 13C NMR (300 MHz, d6-DMSO), δ (ppm): 160.06, 153.73, 143.86, 141.57, 131.87, 130.25, 126.15, 123.14, 121.19, 119.53, 115.99, 79.09, 60.10. CHN analysis: Count: C, 60.39; H, 5.07; N, 4.40; found: C, 60.47; H, 5.063; N, 4.485.

As a result, 4-[(E)-2-(4-hydroxylphenyl)ethenyl]-1-allylpyridinium is obtained by inserting a terminal vinyl group to a pyridine ring of 4-[(E)-2-(4-pyridinyl)ethenyl]phenol obtained in step (a) by refluxing with an allylic halide. The allylic halide used in this step (b) is allyl bromide.

(c) Synthesis of Pyridinium, 4-[(1E)-2-(4-phenoxyl) ethenyl]-1-vinyl-, Inner Salt (The Solvatochromic Functional Monomer)

The step (c) of the synthesis of solvatochromic functional monomer is the synthesis of pyridinium, 4-[(1E)-2-(4-phenoxyl)ethenyl]-1-vinyl-, inner salt, i.e. the solvatochromic functional monomer of the present invention.

Sodium (0.15 g) was added to 5.0 mL of methanol in a 50 mL round bottom flask and the resultant mixture was stirred at room temperature until all the sodium has dissolved to obtain sodium methoxide. 4-[(E)-2-(4-hydroxylphenyl)ethenyl]-1-allylpyridinium bromide (1.6 g) was then added and the mixture turned dark red in color. The mixture was then stirred for a further 30 min and the methanol was removed under reduced pressure. A dark red powder of the pyridinium, 4-[(1E)-2-(4-phenoxyl)ethenyl]-1-vinyl-, inner salt was obtained. Yield 1.65 g, 100%. The product was stored in a desiccator. The NMR results of the final product are as follows.

1H NMR (400 MHz, d6-DMSO), δ (ppm): 8.76 (d, 2H), 8.12 (d, 2H), 7.93 (d, 1H), 7.58 (d, 2H), 7.23 (d, 1H), 6.81 (d, 2H), 6.10-6.17 (m, 1H), 5.32-5.43 (m, 2H), 5.10 (d, 2H).

As a result, the solvatochromic functional monomer of the present invention is obtained by deprotonating a phenolic group of the 4-[(E)-2-(4-hydroxylphenyl)ethenyl]-1-allylpyridinium obtained in step (b) by using an initiator. The initiator used in this step (c) is sodium methoxide.

In summary, the process for preparing the solvatochromic functional monomer of the present invention comprises the following steps of:

(a) coupling 4-hydroxybenzaldehyde with 4-methylpyridine by using a dehydrated reagent for obtaining 4-[(E)-2-(4-pyridinyl)ethenyl]phenol;

(b) inserting a terminal vinyl group to a pyridine ring of 4-[(E)-2-(4-pyridinyl)ethenyl]phenol obtained in step (a) by refluxing with an allylic halide for obtaining 4-[(E)-2-(4-hydroxyphenyl)ethenyl]-1-allylpyridinium; and (c) deprotonating a phenolic group of the 4-[(E)-2-(4-hydroxyphenyl)ethenyl]-1-allylpyridinium obtained in step (b) by using an initiator for obtaining the solvatochromic functional monomer of the present invention.

Figure 1:
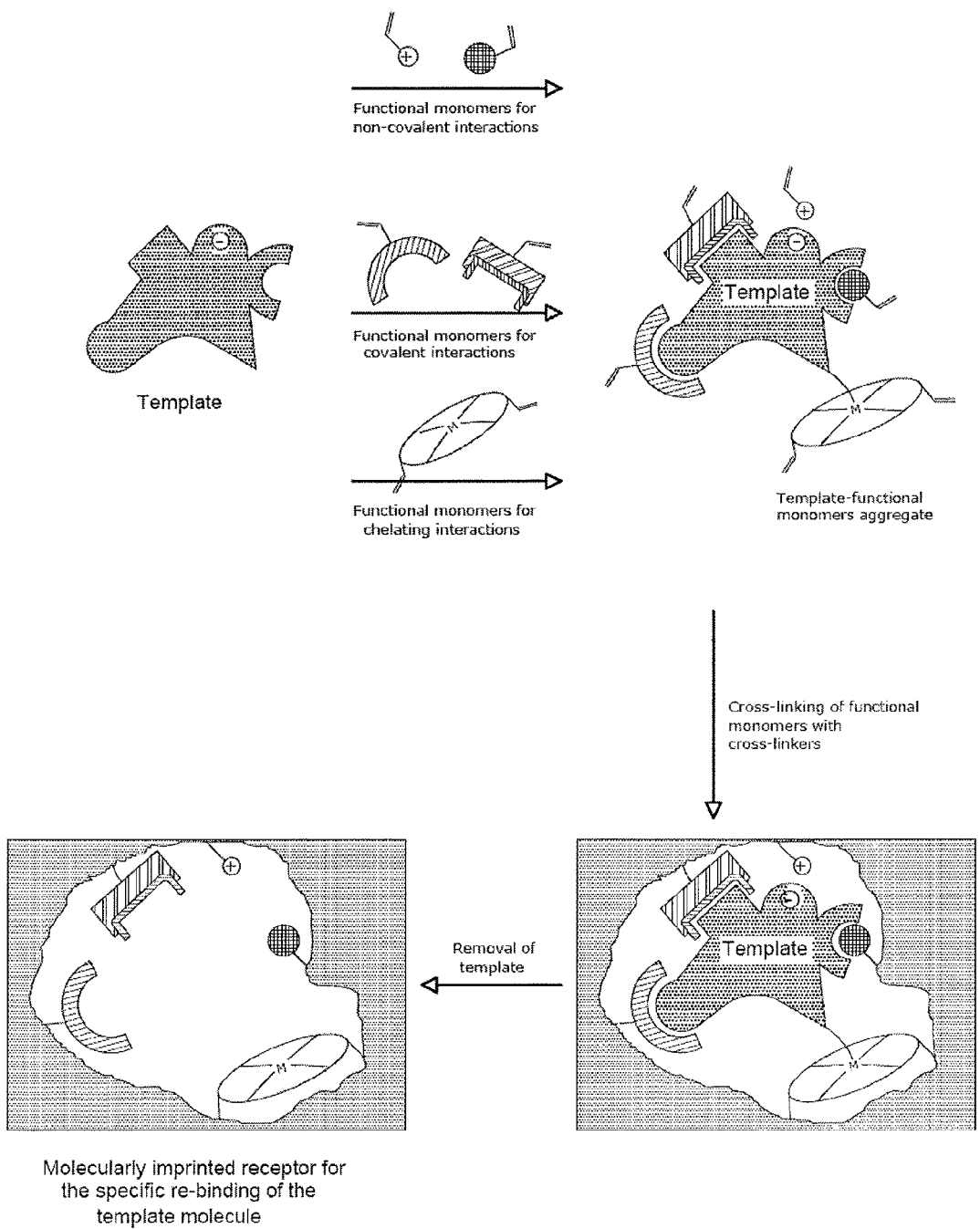
FIG. 1 depicts a schematic representation of the molecular imprinting process.
Figure 2:
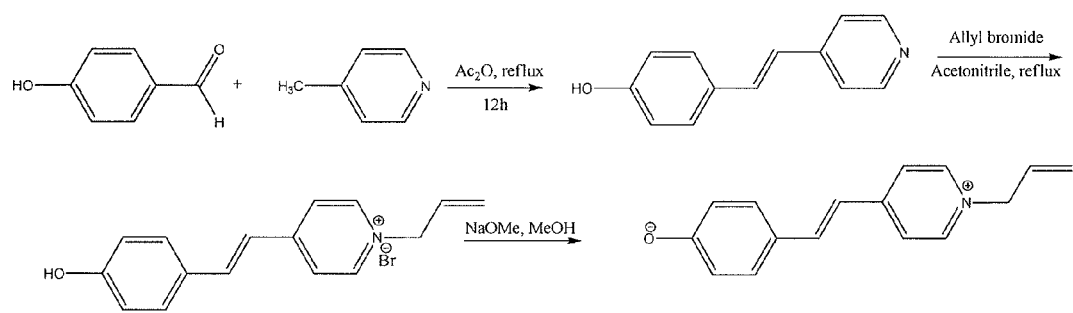
FIG. 2 depicts a synthetic route of the solvatochromic functional monomer.

The dehydrated reagent used in step (a) is acetic anhydride.
The allylic halide used in step (b) is allyl bromide.
The initiator used in step (c) is sodium methoxide.
The synthetic route of the solvatochromic functional monomer is shown in FIG. 2.
The chemical structure of the solvatochromic functional monomer is shown in FIG. 3.

Spectroscopic Characterization of the Solvatochromic Functional Monomer

Spectroscopic characterization of the solvatochromic functional monomer (at 2.0×10-5 M) were performed in various different solvents. Air-tight screw-capped quartz cells of 1.0 cm optical path length were used. Unless stated otherwise in this document, all luminescent spectra were performed with 2.0 mg of molecularly imprinted polymer incorporated with the solvatochromic functional monomer or control polymer material in 3.0 mL of ethanol. The control polymer material do not incorporate with the solvatochromic functional monomer.

Figure 4:
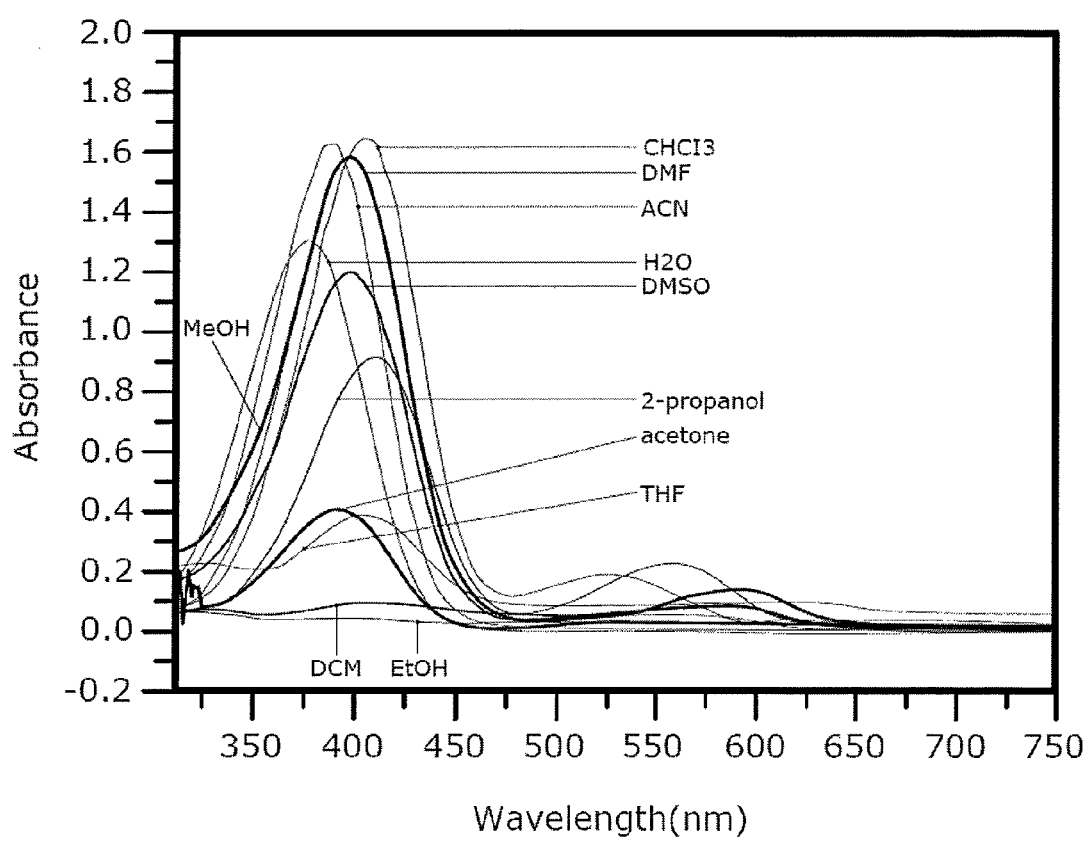
FIG. 4 depicts Ultraviolet and Visible (UV-Vis) spectra of the solvatochromic functional monomer in different solvents.

The ultraviolet and visible (UV-Vis) spectra of the solvatochromic functional monomer in various solvents are shown in FIG. 4. The absorption bands at 300-450 nm and 500-750 nm shifted with solvents of different polarity. This illustrates the solvatochromic properties of the solvatochromic functional monomer. The abbreviations of ACN, DCM, DMF, DMSO, and THF in FIG. 4 stand for acetonitrile, dichloromethane, dimethylformamide, dimethylsulfoxide, and tetrahydrofuran, respectively.

Figure 5:
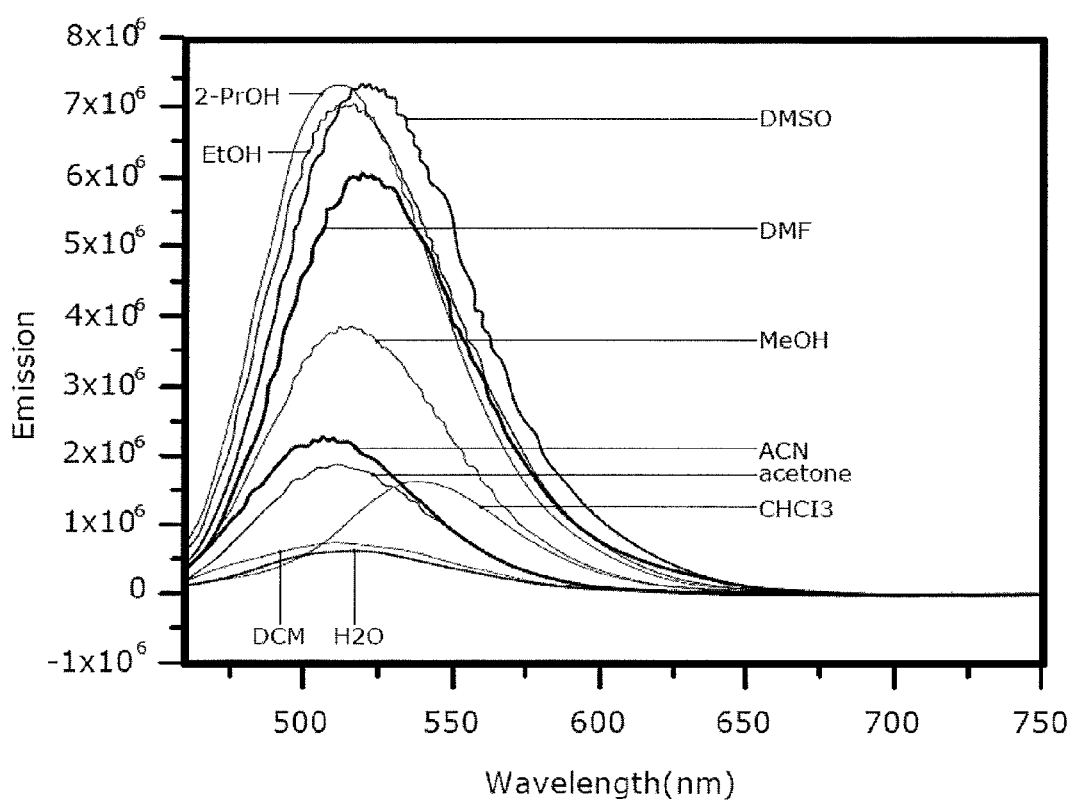
FIG. 5 depicts Emission spectra ($\lambda_{excitation}$=380 nm) of the solvatochromic functional monomer in different solvents.

FIG. 5 shows the emission spectra of the solvatochromic functional monomer in various solvents ($\lambda_{excitation}$=380 nm). The abbreviations of DMF, DMSO, DCM, and ACN have the same meaning as in FIG. 4. The solvatochromic functional monomer also exhibited solvatochromism in its fluorescence. The solvatochromism in fluorescence showed a much clearer trend than that in the absorption spectra. In general, the solvatochromic functional monomer shows much stronger emission in polar solvents.

Next we describe the use of the solvatochromic functional monomer for fabrication of a molecularly imprinted polymer (MIP-based) solvatochromic chemosensor.

Fabrication of Solvatochromic Molecularly Imprinted Polymer

The solvatochromic functional monomer of the present invention (0.12 g, 0.5 mmol) and TBAPF (194.0 mg, 0.5 mmol) were dissolved in 6.0 mL of dimethylsulfoxide (DMSO) in a conical flask. TRIM (678.0 mg, 2.0 mmol) in 6.0 mL of acetonitrile was then added and the mixture was stirred in dark at room temperature for 12 hr. 100 mg of ABCN was then added and the resultant mixture was degassed by bubbling with nitrogen for at least 20 min and sealed under a nitrogen atmosphere by a rubber cap. The mixture was then placed in a 60° C. oil bath for 24 hr. The polymer obtained was filtered and washed with deionized water and methanol and dried over a freeze-drier. The resultant bulk polymer was crushed, milled and wet sieved in methanol through a 48 μm sieve and was collected by centrifugation. TBAPF in the polymer was removed by Soxhlet extraction with 200 ml of a methanol/acetic acid mixture (9:1 v/v) for 24 hr, followed by 200 ml of methanol for 24 hr in dark. The resultant imprinted polymer material was dried to constant weight over a freeze-drier. A total of 0.65 g of orange color polymer material was obtained.

Figure 6:
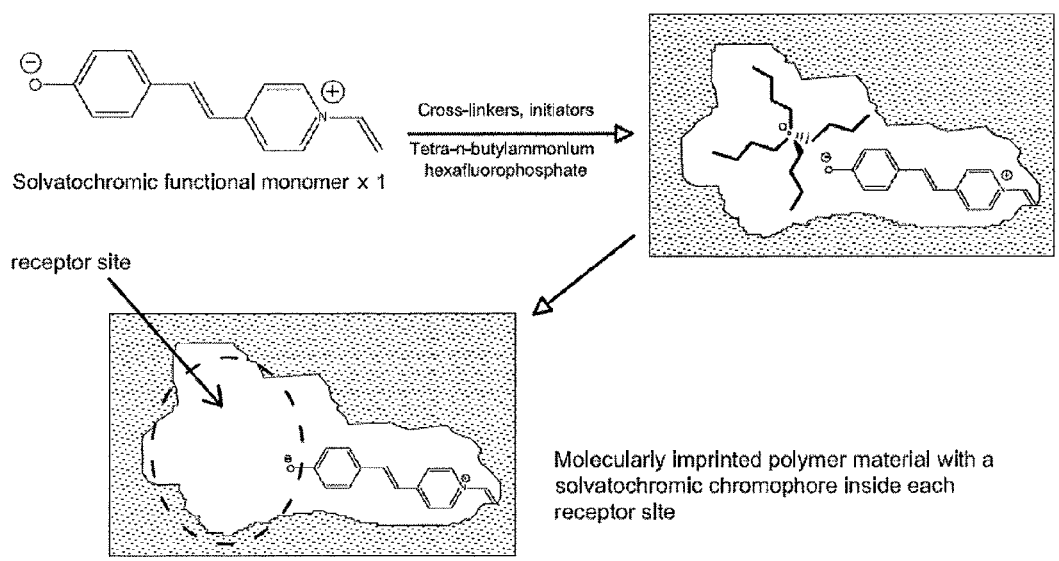
FIG. 6 depicts fabrication of the MIP-based solvatochromic chemosensor for tetra-n-butylammonium cation by the solvatochromic functional monomer.

The solvatochromic functional monomer is zwitterionic, and is not soluble in neat acetonitrile. In the imprinting of TBAPF, a porogen mixture of DMSO and acetonitrile (1:1 v/v) was used. The cross-linker TRIM was used in the MIPs fabrication. Its performance was found to be better than another commonly used cross-linker in molecular imprinting, ethylene glycol dimethacrylate (EDGMA). The optimum monomer:template:cross-linker mole ratio was found to be 1:1:4. The overall MIPs fabrication scheme is shown in FIG. 6.

In summary, the process for preparing a molecularly imprinted polymer based solvatochromic chemosensor comprises the following steps of:

(a) polymerizing a solvatochromic functional monomer and a template by cross-linker for obtaining a molecularly imprinted polymer; and (b) removing the template from the molecularly imprinted polymer obtained in step (a) for obtaining a molecularly imprinted polymer based solvatochromic chemosensor.

The solvatochromic functional monomer used in step (a) is a solvatochromic functional monomer of the present invention.

In this embodiment, the solvatochromic molecularly imprinted polymer is directed to detect an important environmental contaminant, tributyltin (TBT). The tributyltin cannot be used as template in fabricating the solvatochromic molecularly imprinted polymer because of its high toxicity and the fact that it does not participate in common intermolecular interaction. Therefore, its structural mimic, tetra-n-butylammonium cation is used for the fabrication of the MIP-based solvatochromic chemosensor.

It shows that the template used in the process for preparing a molecularly imprinted polymer based solvatochromic chemosensor for a particular analyte can be the analyte itself if the analyte participate in common interaction with the solvatochromic functional monomer. Such interaction includes but not limited to hydrogen bonding, non-polar interactions, dipole-dipole interactions, electron transfer, photo-induced electron transfer, energy transfer and photo-induced energy transfer, etc. In the meantime, the template used in the process for preparing a molecularly imprinted polymer based solvatochromic chemosensor for a particular target analyte can be a chemically structural mimic to the particular target analyte.

Molecularly Imprinted Polymer Based Solvatochromic Chemosensing Approach

Finally we describe the MIP-based solvatochromic chemosensing approach according to the present invention. It is well known that the interaction between the functional monomers used in molecularly imprinted polymers (MIPs) and the targeted analytes is necessary and important in the molecular imprinting process as well as the subsequent analyte rebinding and chemosensing process. Therefore, the MIP-based chemosensing approach of the prior art all require some sort of intermolecular interaction between the analyte and the signal transducer moiety. Intermolecular interactions such as hydrogen bonding, non-polar interactions, dipole-dipole interactions, electron transfer, photo-induced electron transfer, energy transfer and photo-induced energy transfer, etc. have been used for the MIP-based chemosensing approach. In the meantime, the imprinted receptors which function as signal transducer must be capable of convert the receptor-analyte rebinding event into physically measureable signals. However, the signal transduction requirement has posed a technical barrier for the MIP-based chemosensing approach for sensing analytes that do not generally interact with commonly used imprinted receptors (i.e. signal transducers). Examples of these "inert" analytes include polychlorinated biphenyls, dioxins and dibenzofurans, polybrominated diphenyl ethers, organochlorine pesticides, organometallic contaminants such as organotin, organomercury and organoarsenic species and so forth. These analytes lack the ability of intermolecular interaction, and are difficult to be sensed by MIP-based chemosensing approaches of the prior art.

Figure 7:
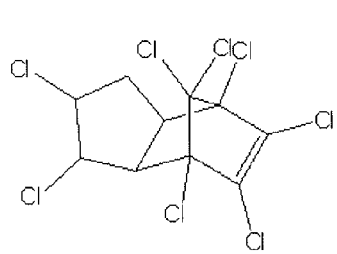
FIG. 7 depicts difficulties encountered in the chemosensing of some of the environmental contaminants.
Figure 7:
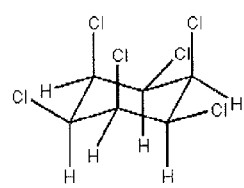
Figure 7:
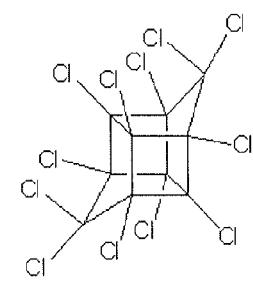
Figure 7:
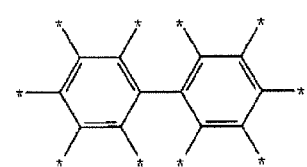
Figure 7:
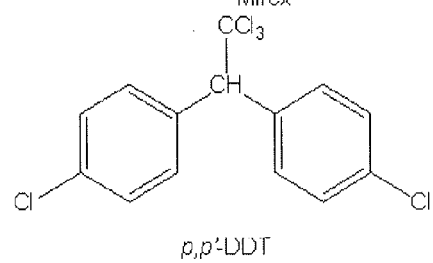
Figure 7:
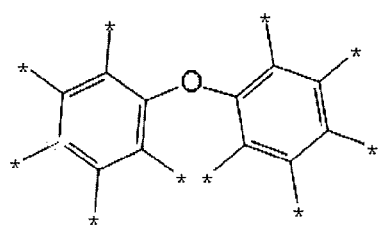
Figure 7:
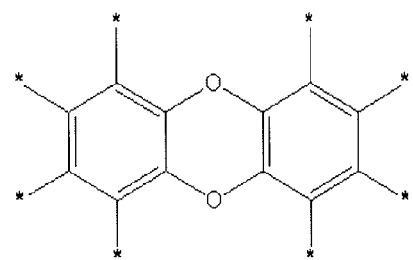

The structure of some of the environmental contaminants which are categorized at "inert" analytes are shown in FIG. 7.

The Applicants have derived a MIPs-based solvatochromic chemosensing approach to circumvent this constraint. This involves the incorporation of a solvatochromic functional monomer as reporter into the molecularly imprinted polymers. The removal of the template results in forming receptor site within the polymer. The solvatochromic functional monomer exhibits a media polarity. So called "solvatochromic" functional monomer means the ability of a functional monomer to change in color or luminescence due to a change in solvent media polarity. The term "solvatochromism" has the similar meaning correspondingly.

On one hand, the solvatochromic functional monomer as reporter is very sensitive to any small change in the media polarity of the micro-environment of the receptor site. On the other hand, the solvatochromic functional monomer as reporter will report the small change of the media polarity in an easily detectable form, e.g. the change in the color and luminescence of the overall MIP-based solvatochromic chemosensor.

Other functional monomer can become a potential candidate for the MIP-based solvatochromic chemosensing approach provided that (1) the functional monomer is sensitive to any small change in the media polarity of the micro-environment; and (2) the functional monomer is capable of converting the small change in the media polarity of the micro-environment into a measurable form, in particular the change in color or luminescent property.

When an analyte enters into the receptor site within the MIP-based solvatochromic chemosensor, the analyte displaces molecule originally accommodated inside the receptor site within the molecularly imprinted polymer. This displacement event generates a change in the media polarity of polymer micro-environment. Electronic transitions of solvatochromic functional monomers, and hence their color and luminescent properties, are very sensitive to the polarity of the solvent media in their surroundings. The change in the media polarity of polymer micro-environment induces spectroscopic and/or luminescent change of the solvatochromic functional monomer. Thus, such displacement can bring about changes in the color and photo-luminescence of the overall MIP-based chemosensor. Accordingly the solvatochromic functional monomer transduces the displacing event into a physically measurable property.

The beauty of this MIP-based solvatochromic chemosensing approach is that no interaction between analytes and the solvatochromic monomer within the imprinted receptor site is needed for chemosensing purposes. Hence, this approach is suitable for the chemosensing of many non-polar analytes that do not bear any specific functional groups that are capable of intermolecular interaction with the functional monomer.

The solvatochromic functional monomer plays important roles in the solvatochromic chemosensing approach and solvatochromic chemosensor due to its ability to change in color and/or luminescence when the media polarity of polymer micro-environment changes.

In summary, in the molecularly imprinted polymer based solvatochromic chemosensing approach, a solvatochromic functional monomer is incorporated into the molecularly imprinted polymer for forming a receptor site within the molecularly imprinted polymer. The solvatochromic functional monomer incorporated in the molecularly imprinted polymer exhibits a media polarity. The media polarity of the solvatochromic functional monomer changes when a target analyte enters into the receptor site. The solvatochromic functional monomer changes in an optical property in response to the change of the media polarity of the solvatochromic functional monomer, so that the overall molecularly imprinted polymer incorporating the solvatochromic functional monomer changes in an optical property when the target analyte enters into the receptor site. The approach comprises the following steps of:

(a) contacting the molecularly imprinted polymer incorporating the solvatochromic functional monomer with a target analyte; and
(b) detecting a change in an optical property of the molecularly imprinted polymer when the target analyte enters into the receptor site within the molecularly imprinted polymer.

The target analyte enters into the receptor site by displacing with a molecule originally accommodated within the receptor site.

The solvatochromic functional monomer incorporated into the molecularly imprinted polymer is the solvatochromic functional monomer of the present invention.

Experimental Testing Results

Figure 8:
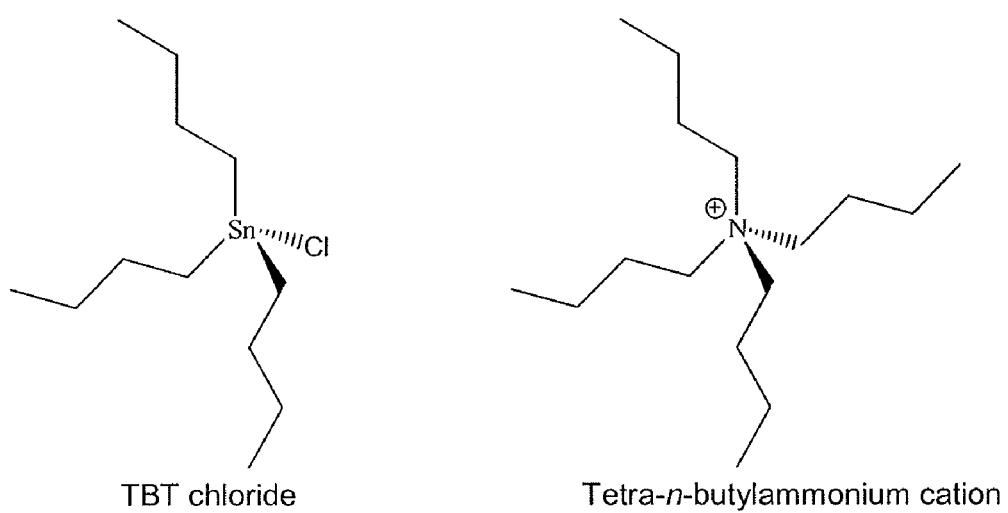
FIG. 8 depicts a comparison of the chemical structure of tributyltin (TBT) and tetra-n-butylammonium cation.

The MIP-based solvatochromic chemosensing approach of the present invention has been tested for an important environmental contaminant, tributyltin (TBT). Tributyltin is considered as toxic chemicals which have negative effects on environment and human. Due to the high toxicity of tributyltin and the fact that it does not participate in common intermolecular interactions, tetra-n-butylammonium cation was used as a structural mimic for the preparation of the MIP-based solvatochromic chemosensor and its test. Reference is made to FIG. 8 for the comparison of the chemical structure of tributyltin (TBT) and tetra-n-butylammonium cation.

The experimental details of fabrication of molecularly imprinted polymer based (MIP-based) solvatochromic chemosensor have been described in section entitled: "Fabrication of solvatochromic molecularly imprinted polymer".

Figure 9A:
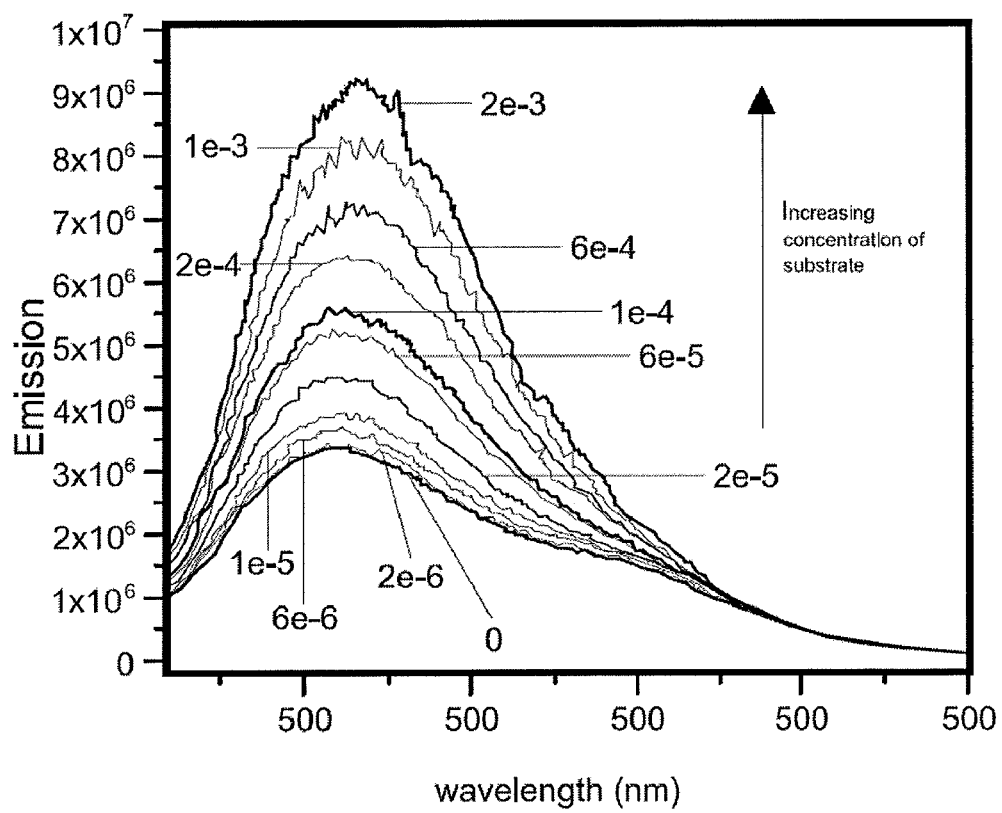
FIG. 9A depicts the luminescence response and FIG. 9B colorimetric depicts the response of the MIP-based solvatochromic chemosensor towards various concentrations of tetra-n-butylammonium cation in ethanol.
Figure 9B:
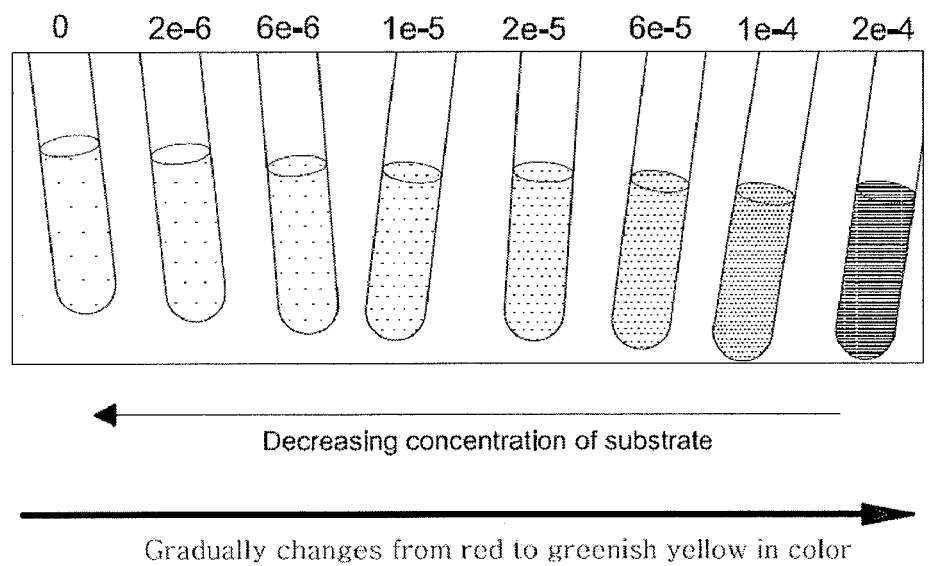

It is certain that the fabricated MIP-based solvatochromic chemosensor is able to produce colorimetric and luminescent response to its tetra-n-butylammonium template in common solvents such as ethanol, as shown in FIG. 9.

The signaling properties of the MIP-based solvatochromic chemosensor and control polymer material (fabricated without the template) were studied in ethanol. Unless otherwise stated, all testing were performed with 2.0 mg of polymer material in 3.0 mL of solution with known amount of substrate at room temperature. In a typical experiment, known amount of tetra-n-butylammonium hexafluorophosphate (TBAPF) was spiked into a series of ethanol suspensions (3.0 mL) of polymer material. These suspensions were then sealed and agitated for 48 hr in dark. Then the mixtures were transferred completely into individual quartz cells for spectrofluorometric measurements. Suspension of the MIP-based solvatochromic chemosensor and control polymer materials was maintained with the help of magnetic stirrers. All luminescent spectra were detected by a Fluorolog TCSPC Horiba Jobin Yvon (FL-1065) spectrofluorometer. Signaling for substrates with chemical structure similar to TBAPF, and tributyltin (TBT) were carried out in exactly the same way.

The luminescence and colorimetric responses are induced by the re-binding of tetra-n-butylammonium cation by the imprinted receptor sites within the MIP-based solvatochromic chemosensor, which displaces solvent molecules out of the receptor sites and perturb the media polarity of the microenvironment inside those sites. This triggers the solvatochromic response of the solvatochromic functional monomer within the receptor sites, which results in the alteration of the overall color and luminescent properties of the MIP-based solvatochromic chemosensor.

Figure 10:
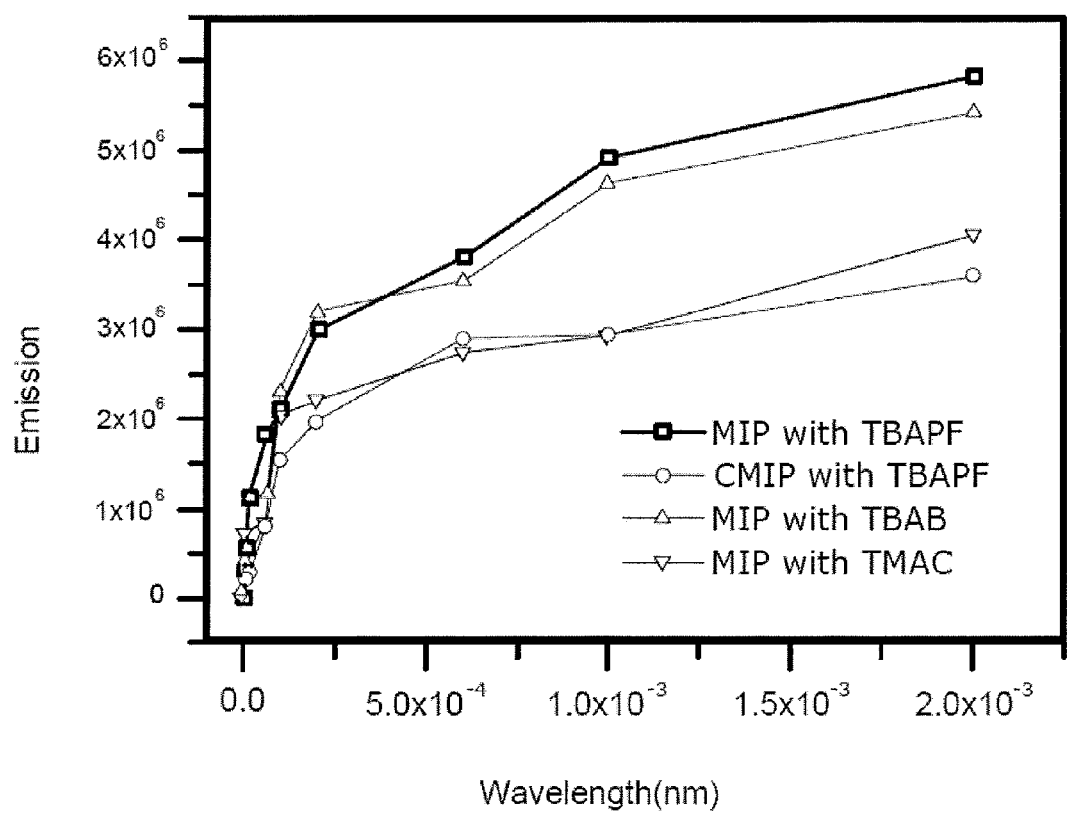
FIG. 10 depicts luminescent responses of the MIPs-based solvatochromic chemosensor and control molecularly imprinted polymer (CMIP) toward different kinds of quaternary ammonium cations.

Such solvatochromic response is quite substrate specific. FIG. 10 shows the luminescent responses of the MIP-based solvatochromic chemosensor as well as the control polymer material (fabricated without the template) towards tetra-n-butylammonium hexafluorophosphate (TBAPF), tetra-n-butylammonium bromide (TBAB) and the structural analog tetramethylammonium chloride (TMAC). It shows that the molecularly imprinted polymer material is capable of specifically recognize the cationic species (disregard of the counter-anions).

Figure 11:
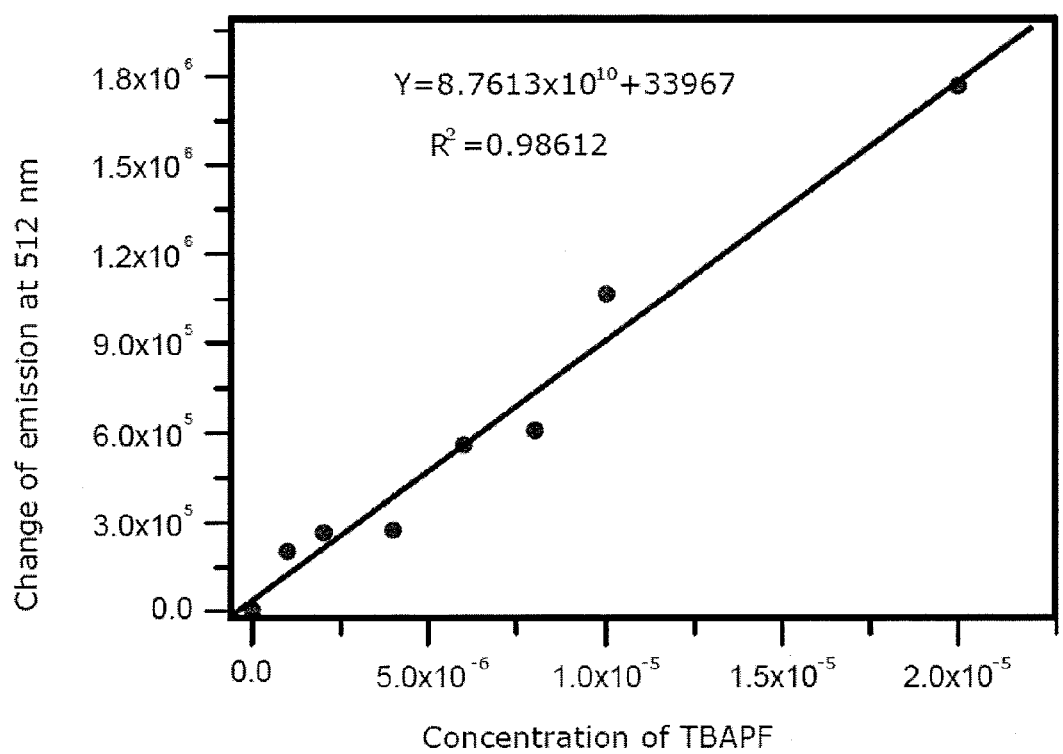
FIG. 11 depicts a linear response of luminescent intensity of the MIP-based solvatochromic chemosensor with the tetra-n-butylammonium cation.

By monitoring the luminescent intensity of the material at 512 nm, a linear response relationship with the concentration of tetra-n-butylammonium cation can be obtained, as shown in FIG. 11. This demonstrates the chemosensing properties of the MIP-based solvatochromic chemosensor.

Figure 12A:
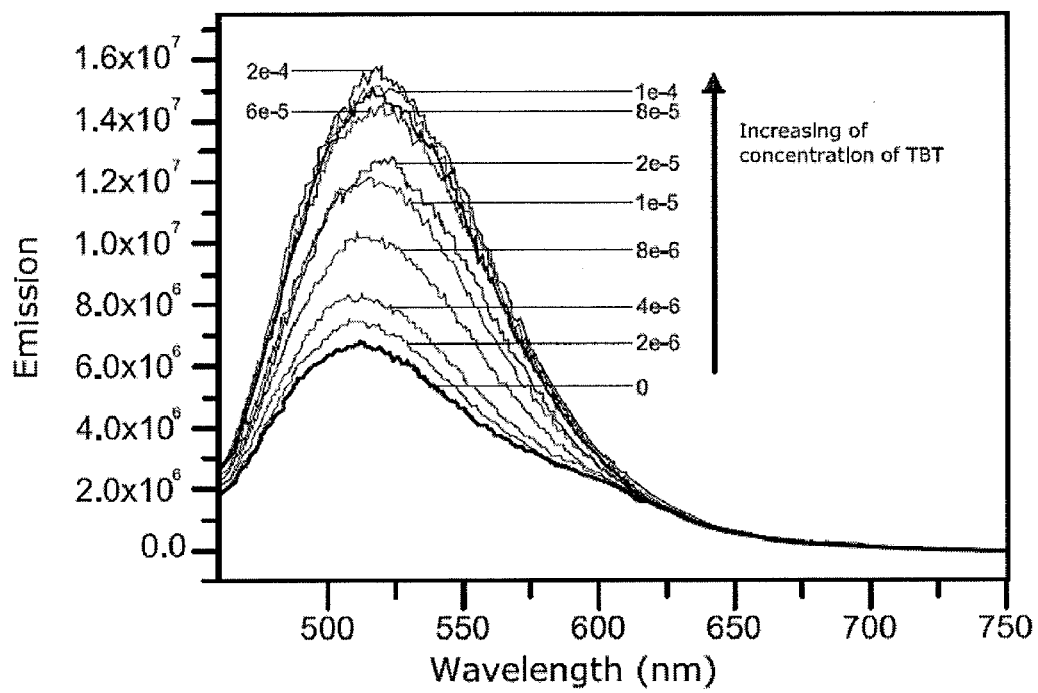
FIG. 12A depicts a luminescent response and FIG. 12B depicts a colorimetric response of the MIP-based solvatochromic chemosensor towards various concentrations of TBT in ethanol.
Figure 12B:
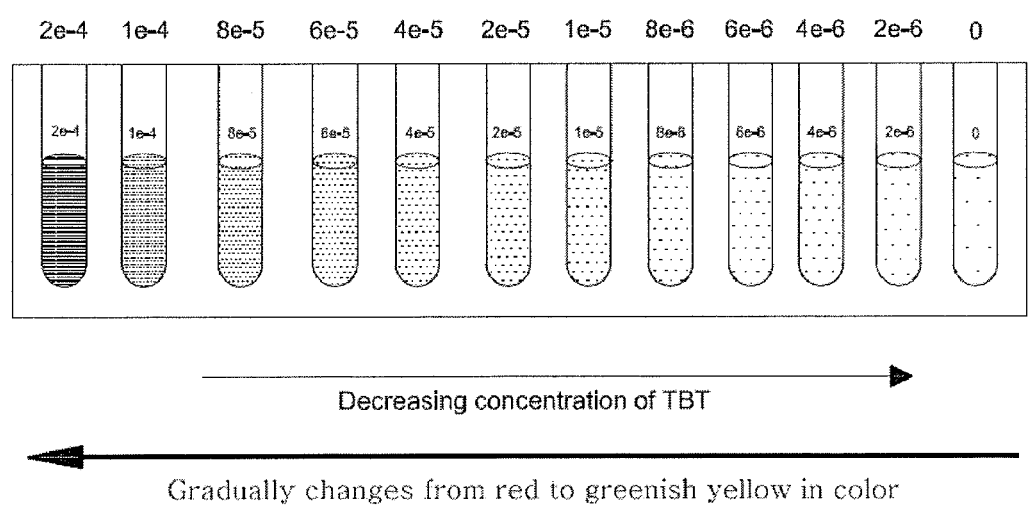

Besides tetra-n-butylammonium cation, the MIP-based solvatochromic chemosensor of the invention can also respond to tributyltin (TBT), as shown in FIG. 12. As mentioned above, the tetra-n-butylammonium cation is just a structural mimic for the imprinting of TBT-recognizing receptor sites in the MIP-based solvatochromic chemosensor. Direct imprinting of TBT with the solvatochromic functional monomer is impractical because of the lack of interaction between the two.

FIG. 12 shows the luminescent and colorimetric responses of the MIP-based solvatochromic chemosensor towards tributyltin (TBT). It is clear that the responses are quite similar to that of the tetra-n-butylammonium template. This has actually demonstrated the feasibility of the MIP-based solvatochromic chemosensing approach of the present invention in which a structural mimic of a non-polar, non-interacting targeted analytes can be used to imprint solvatochromic receptor sites that can recognize the targeted analytes.

Figure 13:
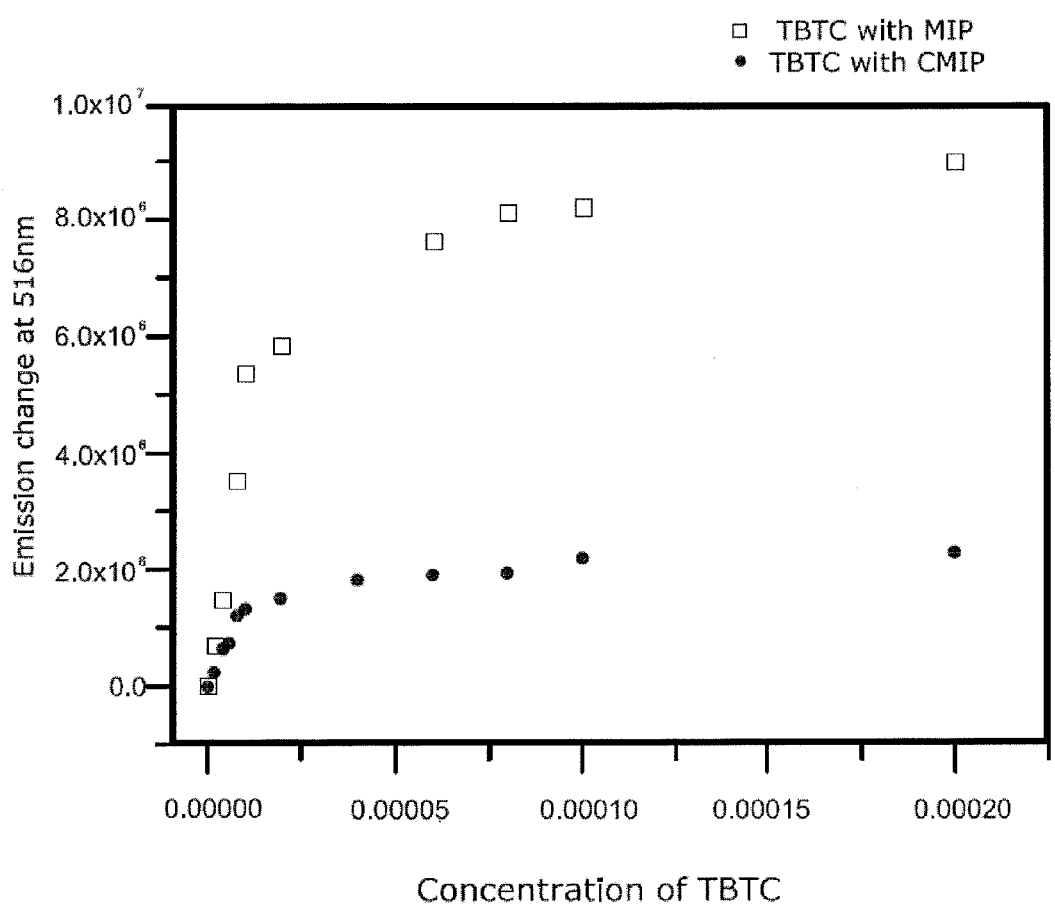
FIG. 13 depicts luminescent responses of the MIP-based solvatochromic chemosensor and control MIP- (or CMIP)-based chemosensor at different concentrations of TBT chloride (TBTC).

FIG. 13 shows the relative luminescent responses of the MIP-based solvatochromic chemosensor and control polymer materials at 516 nm towards TBT chloride. Even though the control polymer material also possesses the solvatochromic functional monomers, its response towards TBT is much smaller compared to the MIP-based solvatochromic chemosensor. This is because of the fact that the control material does not have receptor sites that allow the displacement of TBT.

All the above demonstrate the industrial application of the MIP-based solvatochromic chemosensing approach for the molecularly imprinted chemosensing of non-polar, non-interacting analytes such as those non-polar environmental contaminants, which are well-known to be very difficult candidates for chemosensing.

While the present invention has been described by way of example and in terms of the preferred embodiments, it is to be understood that the present invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

The invention claimed is:

1. A process for preparing a molecularly imprinted polymer based solvatochromic chemosensor, the process comprising the steps of:
(a) polymerizing a solvatochromic functional monomer in the presence of a template by a cross-linker to obtain a molecularly imprinted polymer; and
(b) removing the template from the molecularly imprinted polymer obtained in step (a) to obtain a molecularly imprinted polymer based solvatochromic chemosensor;
wherein the solvatochromic functional monomer comprises the following structure:

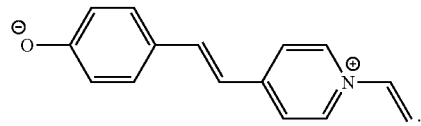

2. The process of claim 1, wherein the template of step (a) comprises a structural mimic of a target analyte.

3. The process of claim 2, wherein the structural mimic of the target analyte comprises tetra-n-butylammonium cation.

4. The process of claim 2, wherein the target analyte comprises tributyltin.

5. The process of claim 1, wherein the template of step (a) comprises a target analyte.

6. The process of claim 1, wherein the mole ratio of the monomer: the template: the cross-linker in step (a) is 1:1:4.

* * * * *